United States Patent
Wang et al.

(10) Patent No.: US 9,003,875 B2
(45) Date of Patent: Apr. 14, 2015

(54) SHEET THICKNESS DETECTION APPARATUS FOR DETECTING DIFFERENT MAXIMUM ALLOWABLE THICKNESSES OF PLURAL PAPERS USING MOVABLE SENSING DEVICE

(75) Inventors: Chung-Kai Wang, Taipei (TW); Chung-Jung Chiu, Taipei (TW); Wen-Lung Hung, Taipei (TW)

(73) Assignee: Primax Electronics Ltd., Taipei (TW)

( * ) Notice: Subject to any disclaimer, the term of this patent is extended or adjusted under 35 U.S.C. 154(b) by 296 days.

(21) Appl. No.: 13/586,594

(22) Filed: Aug. 15, 2012

(65) Prior Publication Data
US 2013/0276526 A1    Oct. 24, 2013

(30) Foreign Application Priority Data
Apr. 20, 2012    (TW) .............................. 101114173 A

(51) Int. Cl.
G01L 5/04    (2006.01)
G01N 33/34    (2006.01)

(52) U.S. Cl.
CPC .................................. *G01N 33/346* (2013.01)

(58) Field of Classification Search
CPC ...... G01N 33/346; B65H 43/06; B65H 31/26; B65H 43/08; B65H 7/02; B65H 2403/531; B65H 2511/152; B65H 2511/214; B65H 2511/514; B65H 2553/412; B65H 2553/612; B65H 2801/27; B65H 2220/03; B65H 2220/01; B65H 2220/11; B42C 1/12; G01B 5/06
USPC ....................... 73/159; 198/323; 33/549, 833; 270/58.09
See application file for complete search history.

(56) References Cited

U.S. PATENT DOCUMENTS

| | | | | |
|---|---|---|---|---|
| 5,236,075 | A | * | 8/1993 | Bartmann ..................... 198/323 |
| 8,495,821 | B2 | * | 7/2013 | Wang .............................. 33/549 |
| 2013/0276526 | A1 | * | 10/2013 | Wang et al. .................... 73/159 |

* cited by examiner

*Primary Examiner* — Hezron E Williams
*Assistant Examiner* — Truong Phan
(74) *Attorney, Agent, or Firm* — Kirton McConkie; Evan R. Witt

(57) ABSTRACT

A sheet thickness detection apparatus includes a bracket, a power device, a first linking lever, a second linking lever, a sheet pressing part, and a sensing device. The bracket has a base with a perforation. The sensing device includes a supporting part and a sensor. The power device, the first linking lever, the second linking lever and the sheet pressing part are disposed on a first surface of the bracket. The sensor is fixed on the supporting part. When the supporting part is connected to a second surface of the base, the sensor is penetrated through the perforation and exposed to a lateral side of the first linking lever. Moreover, the supporting part is movable, so that the position of the sensor relative to the first linking lever is adjustable.

20 Claims, 16 Drawing Sheets

SHEET THICKNESS DETECTION APPARATUS FOR DETECTING DIFFERENT MAXIMUM ALLOWABLE THICKNESSES OF PLURAL PAPERS USING MOVABLE SENSING DEVICE

FIELD OF THE INVENTION

The present invention relates to a sheet thickness detection apparatus, and more particularly to a sheet thickness detection apparatus for an office machine.

BACKGROUND OF THE INVENTION

An office machine such as a printer or a scanner is widely used in the office. For achieving diversified functions and integrating more functions, the office machine is usually equipped with a post-processing apparatus. For example, the post-processing apparatus is a stapling apparatus, a punching apparatus, or the like. Before the paper sheets are outputted from the office machine, the paper sheets are automatically processed by the post-processing apparatus according to the user's requirements. Due to the limitations of the specifications of the stapling apparatus or the punching apparatus, if the thickness of the paper sheets on the sheet placement platform exceeds the allowable range of the stapling apparatus or the punching apparatus, the paper sheets are readily suffered from injury and even the post-processing apparatus is possibly damaged. For solving these drawbacks and minimizing the erroneous operations of the post-processing apparatus, a sheet thickness detection apparatus is required to assure that the thickness of the paper sheets on the sheet placement platform is smaller than the maximum allowable thickness.

Hereinafter, the structure of a conventional sheet thickness detection apparatus will be illustrated with reference to FIGS. 1 and 2. FIG. 1 is a schematic perspective view illustrating a conventional sheet thickness detection apparatus. FIG. 2 is a schematic exploded view illustrating the conventional sheet thickness detection apparatus of FIG. 1. As shown in FIGS. 1 and 2, the conventional sheet thickness detection apparatus 1 comprises a power device 11, a first linking lever 12, a second linking lever 13, a sheet pressing part 14, a sensing device 15, and a bracket 16.

Moreover, the power device 11 comprises a coil bobbin 111, a plunger 112, and a positioning plate 113. The coil bobbin 111 has a channel 111a. The first linking lever 12 has a notch 121. The sensing device 15 comprises an emitting terminal 151 and a receiving terminal 152. The bracket 16 has a shaft 161. The shaft 161 is integrally formed with the bracket 16.

A sequence of assembling the conventional sheet thickness detection apparatus will be illustrated in more details as follows.

The plunger 112 of the power device 11 is inserted into the channel 111a of the coil bobbin 111. A distal end of the plunger 112 is exposed outside the coil bobbin 111. The positioning plate 113 is arranged around the distal end of the plunger 112. The first linking lever 12 is connected with the distal end of the plunger 112. In addition, a first end of the second linking lever 13 is connected with the first linking lever 12, and a second of the second linking lever 13 is pivotally coupled to the shaft 161 of the bracket 16. The sheet pressing part 14 is extended from the second of the second linking lever 13, and perpendicular to the second linking lever 13. In addition, the sheet pressing part 14 is integrally formed with the second linking lever 13. The emitting terminal 151 and the receiving terminal 152 of the sensing device 15 are located at bilateral sides of the first linking lever 12, respectively. Furthermore, the power device 11 and the sensing device 15 are fixed on the bracket 16.

Hereinafter, the operating principles of the conventional sheet thickness detection apparatus will be illustrated with reference to FIGS. 3 and 4. FIG. 3 is a schematic side view illustrating the conventional sheet thickness detection apparatus, in which the thickness of the plural paper sheets does not exceed the maximum allowable thickness. FIG. 4 is a schematic side view illustrating the conventional sheet thickness detection apparatus, in which the thickness of the plural paper sheets exceeds the maximum allowable thickness.

When a paper sheet S is about to be introduced into the sheet placement platform 17, a controller (not shown) may enable the power device 11 to drive movement of the plunger 112 of the power device 11. As the plunger 112 of the power device 11 is moved, the first linking lever 12 is linked to be horizontally moved in the direction toward the coil bobbin 111 until the positioning plate 113 is contacted with the coil bobbin 111. Consequently, the second linking lever 13 is linked to be rotated in a direction distant from the sheet placement platform 17 relative to the shaft 161. Meanwhile, the sheet pressing part 14 is raised to allow the paper sheet S to be introduced into the sheet placement platform 17.

After the paper sheet S is introduced into the sheet placement platform 17, the controller (not shown) disables the power device 11. Consequently, the sheet pressing part 14 and the second linking lever 13 are rotated in a direction toward the sheet placement platform 17 relative to the shaft 161 until the paper sheet S on the sheet placement platform 17 is pressed by the sheet pressing part 14.

Furthermore, the power device 11 is alternately enabled and disabled by the controller (not shown) until the plural paper sheets S to be stapled or punched are all introduced into the sheet placement platform 17.

If the thickness of the plural paper sheets S on the sheet placement platform 17 does not exceed the maximum allowable thickness, the signal emitted by the emitting terminal 151 of the sensing device 15 can be transmitted to the receiving terminal 152 of the sensing device 15 through the notch 121 of the first linking lever 12 (see FIG. 3). Under this circumstance, the controller judges that the thickness of the plural paper sheets S does not exceed the maximum allowable thickness. Consequently, the controller will start the subsequent stapling or punching operation.

On the other hand, if the thickness of the plural paper sheets S exceeds the maximum allowable thickness, the signal emitted by the emitting terminal 151 of the sensing device 15 is hindered by the first linking lever 12 (see FIG. 4). Accordingly, the controller will stop the stapling or punching operation.

However, the conventional sheet thickness detection apparatus 1 still has the following drawbacks. For example, due to the limitations of the specifications of different stapling apparatuses or punching apparatuses, the maximum allowable thicknesses for different stapling apparatuses or different punching apparatuses are usually distinguished. Since the power device 11 and the sensing device 15 are fixed on the bracket 16, the sensing device 15 of the conventional sheet thickness detection apparatus 1 is immobile. Under this circumstance, the controller will determine whether the subsequent stapling or punching operation of the stapler or stapling apparatus or the punching apparatus is performed according to a specified maximum allowable thickness. In other words, the sheet thickness detection apparatus 1 fails to comply with the stapling apparatuses or punching apparatuses of various specifications.

From the above discussions, if the manufacturer wants to develop a sheet thickness detection apparatus complying with the post-processing apparatuses of various specifications, the sheet thickness detection apparatus should be equipped with plural sensing devices at different positions according to the respective maximum allowable thicknesses. Under this circumstance, the fabricating process is very complicated.

Therefore, there is a need of providing an improved sheet thickness detection apparatus in order to eliminate the drawbacks encountered from the prior art.

SUMMARY OF THE INVENTION

The present invention relates to a modular sheet thickness detection apparatus with a movable sensing device.

In accordance with an aspect of the present invention, there is provided a sheet thickness detection apparatus for detecting a thickness of plural paper sheets on a sheet placement platform. The sheet thickness detection apparatus has a maximum allowable thickness. The sheet thickness detection apparatus includes a bracket, a power device, a first linking lever, a second linking lever, a sheet pressing part, and a sensing device. The bracket includes a base with a perforation. The power device is fixed on a first surface of the base. The first linking lever is connected with the power device and driven by the power device to be moved. In addition, the first linking lever has a notch. The second linking lever has a first end and a second end. As the first linking lever is moved, the second linking lever is correspondingly swung. The first end of the second linking lever is pivotally coupled with the first linking lever. The sheet pressing part is extended from the second end of the second linking lever and simultaneously swung with the second linking lever. The sensing device includes a supporting part and a sensor. The supporting part is connected to a second surface of the base. The sensor is fixed on the supporting part and penetrated through the perforation from the second surface of the base, so that the sensor is exposed to a lateral side of the first linking lever to detect whether the thickness of the plural paper sheets exceeds the maximum allowable thickness or not. By moving the supporting part, the sensor is moved to a position where the maximum allowable thickness is detectable.

In an embodiment, the supporting part includes three hooks, and the base further includes three sliding grooves. When the supporting part is connected with the base, the three hooks are respectively embedded into the three sliding grooves, so that the supporting part is only permitted to be moved in a direction parallel with the first linking lever.

In an embodiment, the supporting part has a first fixing hole and a first adjusting hole, wherein the first fixing hole and the first adjusting hole are both elliptic.

In an embodiment, the base further includes a second fixing hole and a second adjusting hole. The second fixing hole is overlapped with the first fixing hole, so that the supporting part is connected to the second surface of the bracket through the first fixing hole and the second fixing hole. The second adjusting hole is overlapped with the first adjusting hole.

In an embodiment, when the first linking lever is driven by the power device to be moved in a first direction, the second linking lever is linked by the first linking lever, so that the sheet pressing part is swung in a direction distant from the sheet placement platform.

In an embodiment, the sheet thickness detection apparatus further includes an elastic element, wherein a distal end of the elastic element is sustained against the sheet pressing part.

In an embodiment, when the first linking lever is not driven by the power device, the sheet pressing part is swung in a direction distant toward the sheet placement platform through the elastic element.

In an embodiment, the sensor includes an emitting terminal and a receiving terminal, wherein the emitting terminal and the receiving terminal are located at two opposite sides of the first linking lever, respectively.

In an embodiment, when the plural paper sheets on the sheet placement platform are pressed by the sheet pressing part, if the thickness of plural paper sheets does not exceed the maximum allowable thickness, a signal emitted by the emitting terminal of the sensor is transmitted to the receiving terminal of the sensor through the notch of the first linking lever.

In an embodiment, when the plural paper sheets on the sheet placement platform are pressed by the sheet pressing part, if the thickness of plural paper sheets exceeds the maximum allowable thickness, the signal emitted by the emitting terminal of the sensor is hindered by the first linking lever.

In an embodiment, the bracket further includes a side plate and a shaft. The side plate is perpendicular to the base. The shaft is protruded from the side plate. The second end of the second linking lever is pivotally coupled to the shaft, and the second linking lever is permitted to be swung relative to the shaft.

In an embodiment, the power device includes a coil bobbin, a plunger, and a positioning plate. The coil bobbin is fixed on the first surface of the base, and having a channel. The plunger has a first end accommodated within the channel and a second end exposed outside the coil bobbin. The positioning plate is arranged around the second end of the plunger.

In an embodiment, the first linking lever is connected with the second end of the plunger.

In an embodiment, the sheet pressing part is integrally formed with the second linking lever. In addition, an included angle between the sheet pressing part and the second linking lever is approximately 90 degrees.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

The present invention provides a sheet thickness detection apparatus for use in an office machine with a post-processing apparatus. The sheet thickness detection apparatus is capable of detecting a thickness of plural paper sheets on a sheet placement platform.

Figure 1:
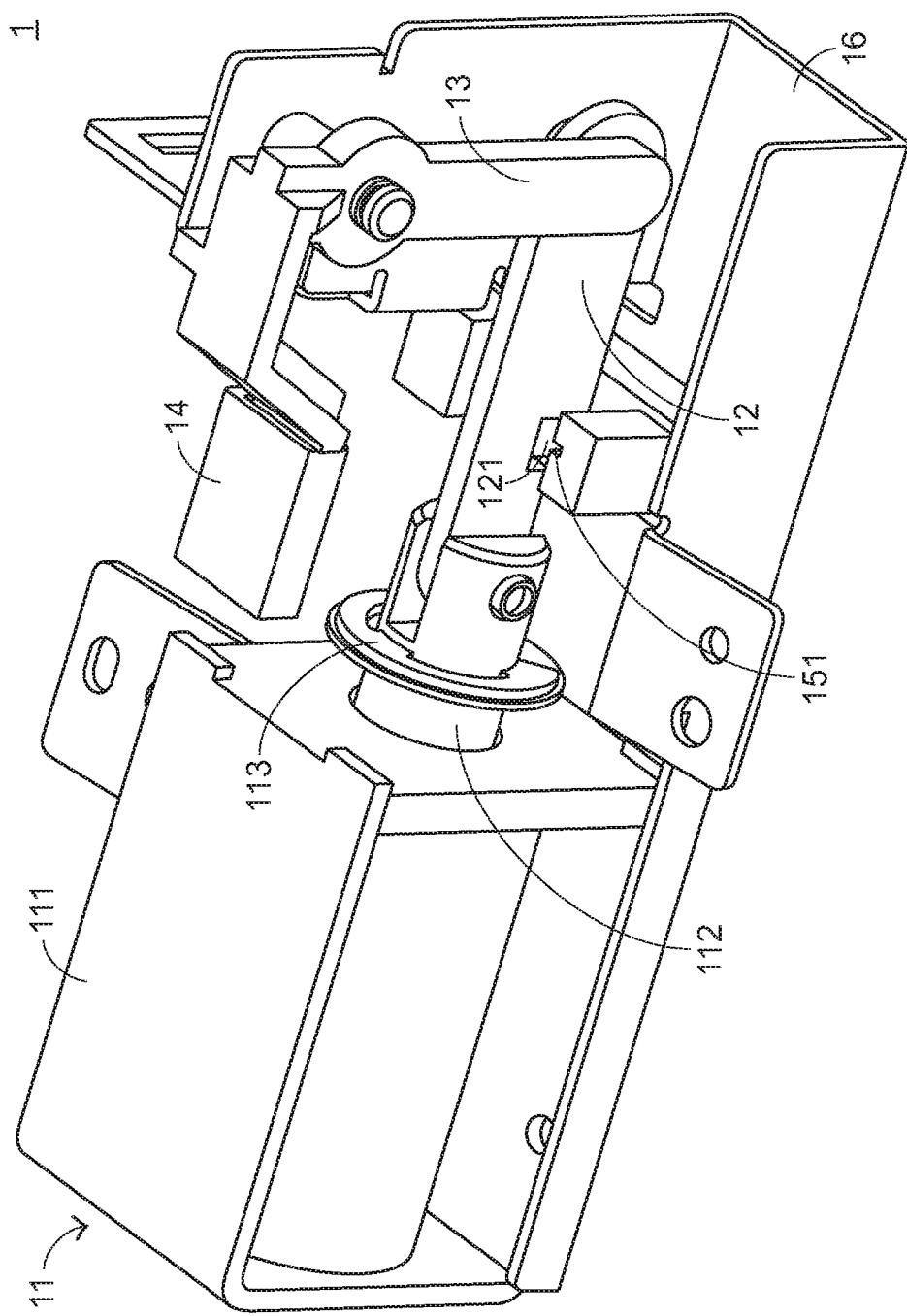
FIG. 1 is a schematic perspective view illustrating a conventional sheet thickness detection apparatus.
Figure 2:
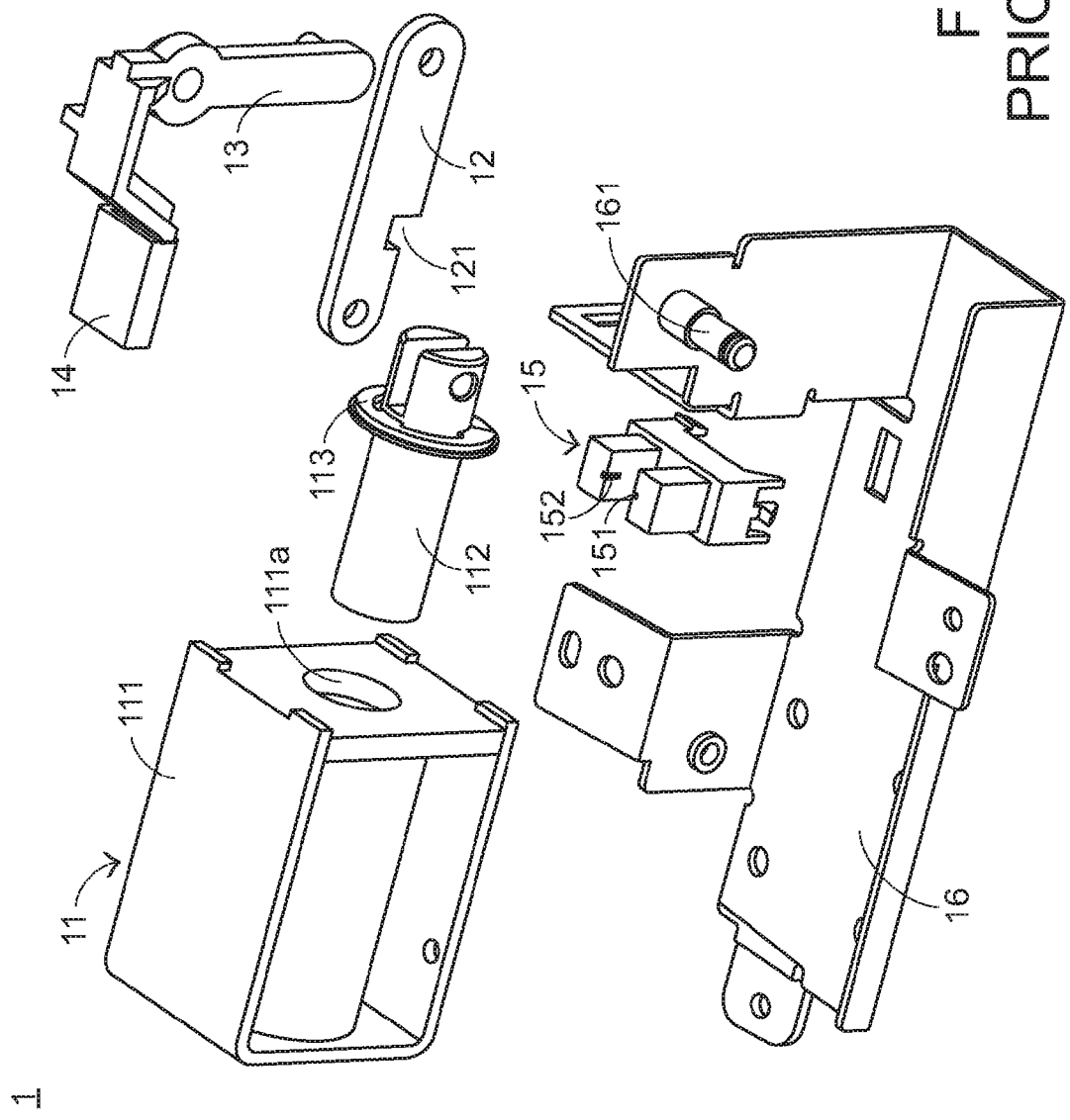
FIG. 2 is a schematic exploded view illustrating the conventional sheet thickness detection apparatus of FIG. 1.
Figure 3:
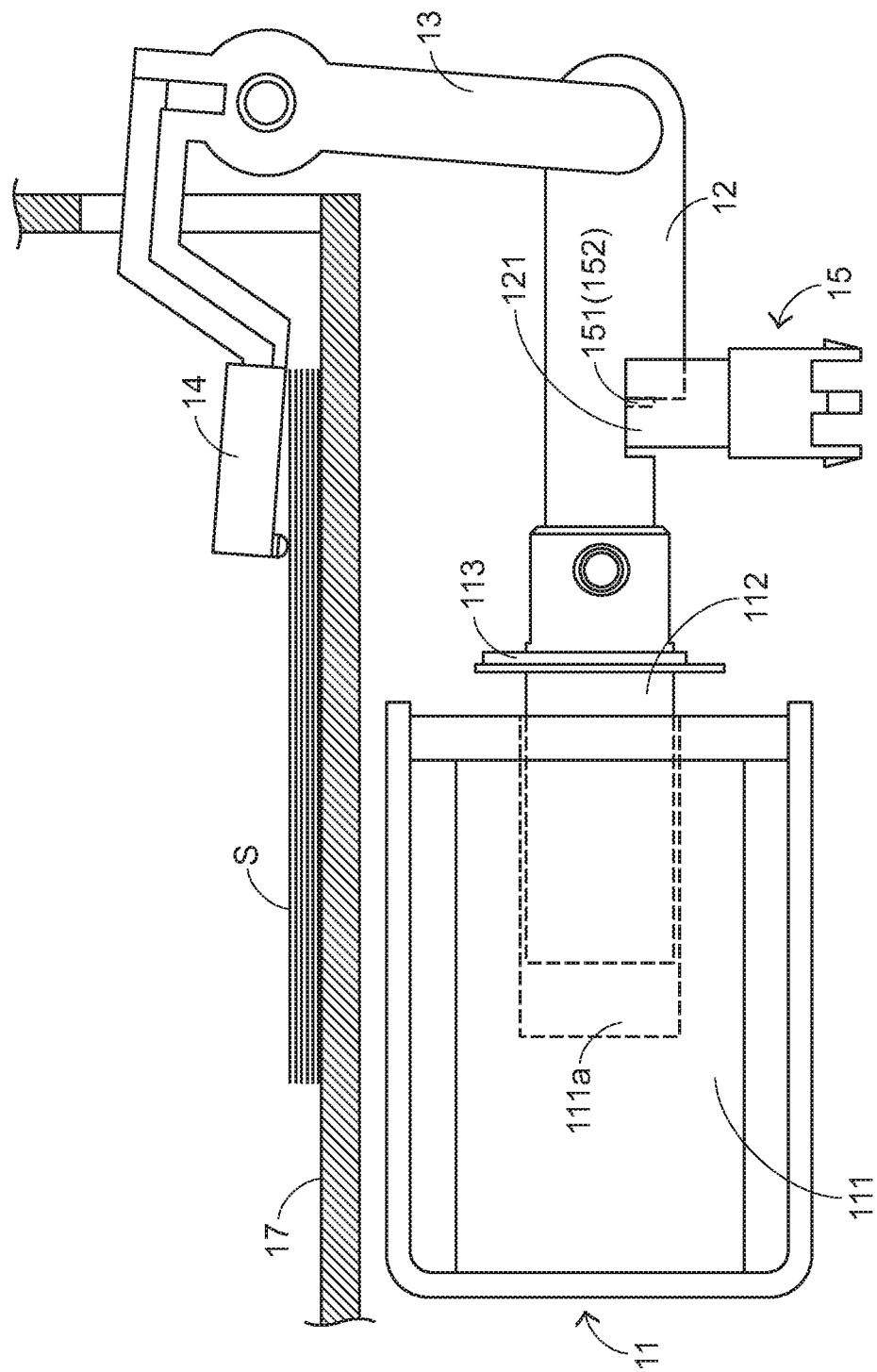
FIG. 3 is a schematic side view illustrating the conventional sheet thickness detection apparatus, in which the thickness of the plural paper sheets does not exceed the maximum allowable thickness.
Figure 4:
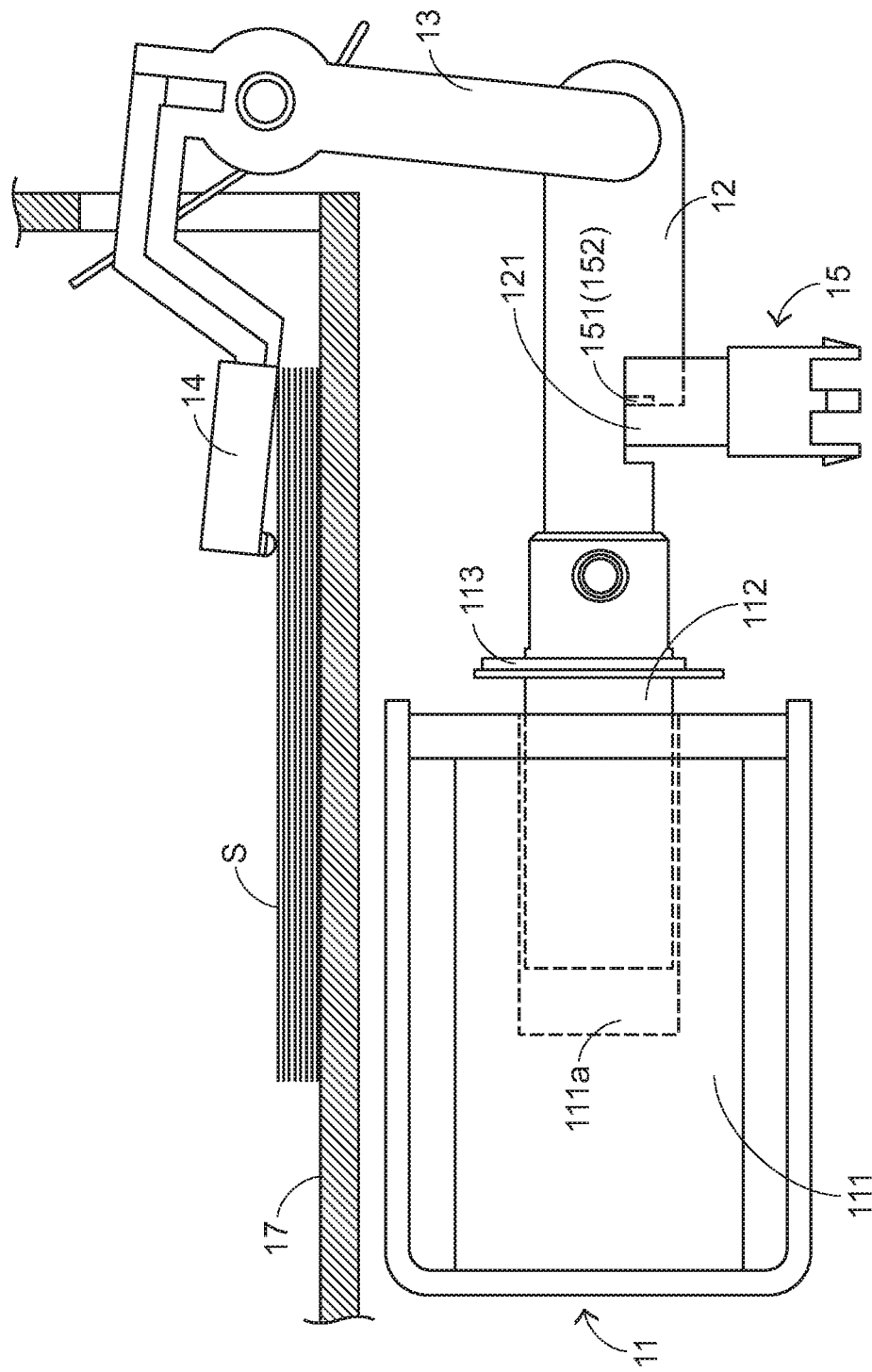
FIG. 4 is a schematic side view illustrating the conventional sheet thickness detection apparatus, in which the thickness of the plural paper sheets exceeds the maximum allowable thickness.
Figure 5:
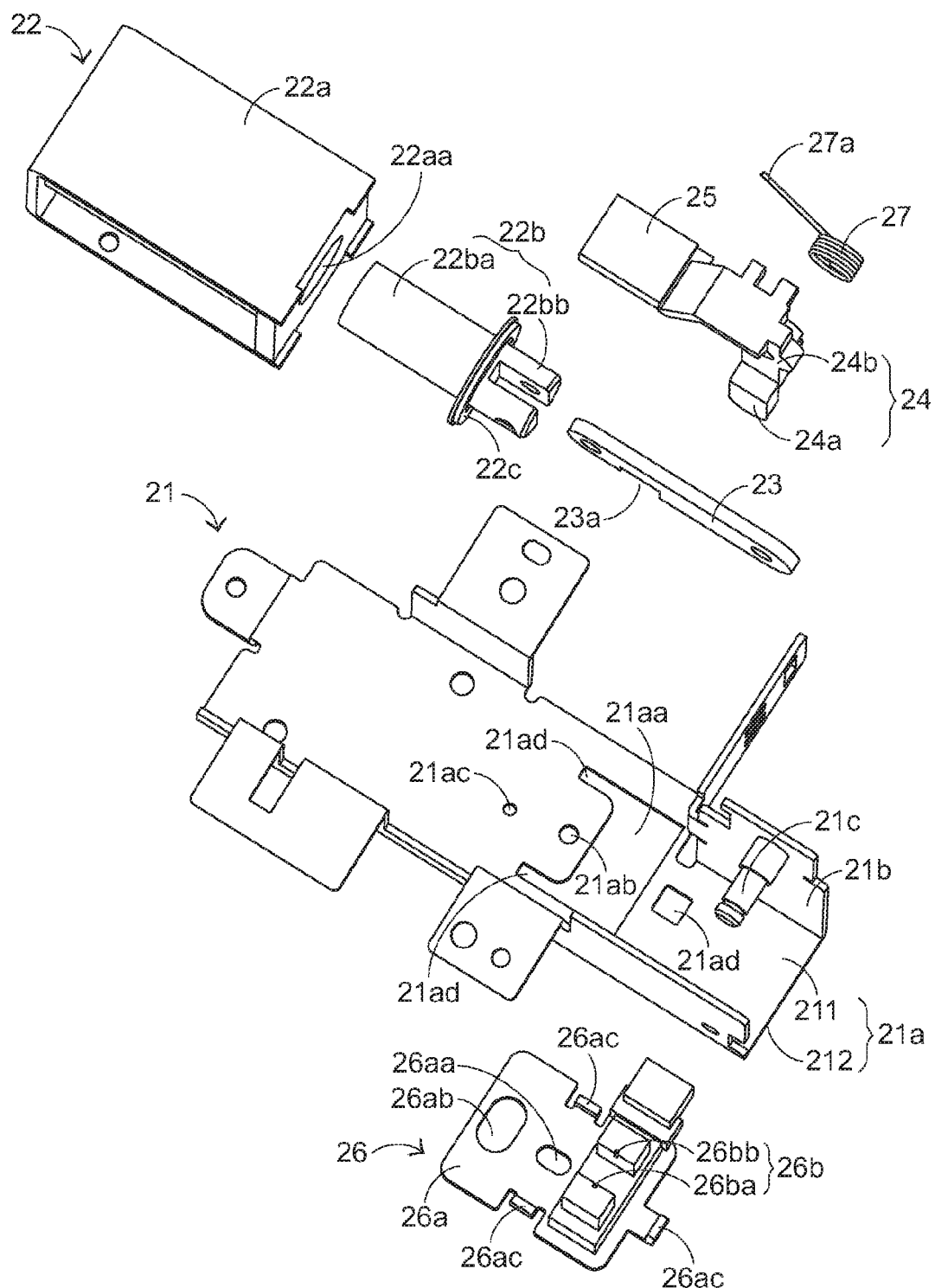
FIG. 5 is a schematic exploded view illustrating a sheet thickness detection apparatus according to an embodiment of the present invention.

Hereinafter, the components of a sheet thickness detection apparatus according to an embodiment of the present invention will be illustrated with reference to FIG. 5. FIG. 5 is a schematic exploded view illustrating a sheet thickness detection apparatus according to an embodiment of the present invention.

As shown in FIG. 5, the sheet thickness detection apparatus 2 comprises a bracket 21, a power device 22, a first linking lever 23, a second linking lever 24, a sheet pressing part 25, a sensing device 26, and an elastic element 27.

The bracket 21 comprises a base 21a, a side plate 21b, and a shaft 21c. The base 21a has a perforation 21aa, a second fixing hole 21ab, a second adjusting hole 21ac, and three sliding grooves 21ad. The power device 22 comprises a coil bobbin 22a, a plunger 22b, and a positioning plate 22c. The coil bobbin 22a has a channel 22aa. The first linking lever 23 has a notch 23a. The sensing device 26 comprises a supporting part 26a and a sensor 26b. The supporting part 26a has a first fixing hole 26aa, a first adjusting hole 26ab, and three hooks 26ac. The sensor 26b comprises an emitting terminal 26ba and a receiving terminal 26bb.

Moreover, in this embodiment, the first fixing hole 26aa and the first adjusting hole 26ab are both elliptic. Moreover, the sheet pressing part 25 is integrally formed with the second linking lever 24, and an included angle between the sheet pressing part 25 and the second linking lever 24 is approximately 90 degrees.

Figure 6:
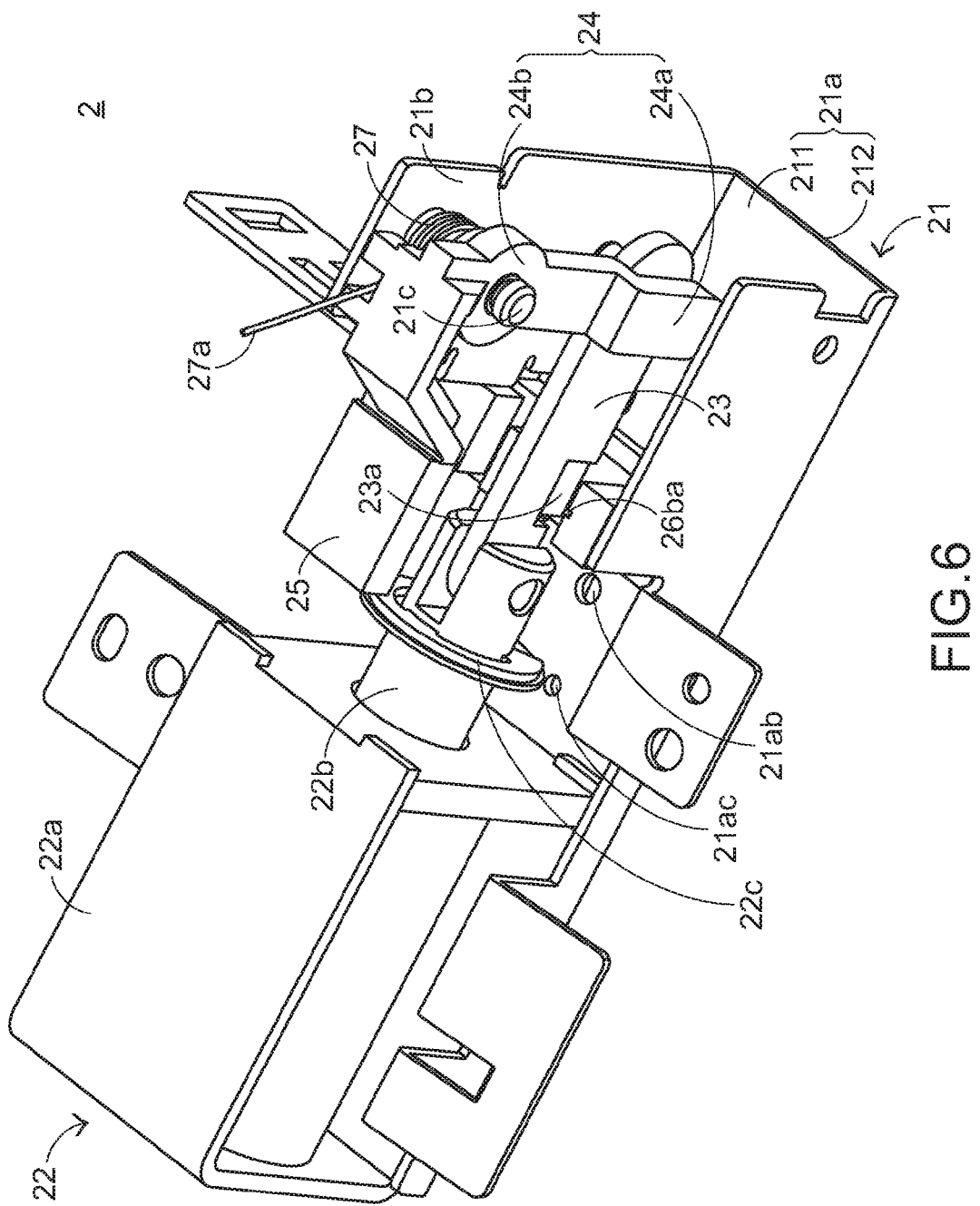
FIG. 6 is a schematic perspective view illustrating the sheet thickness detection apparatus of FIG. 5.
Figure 7:
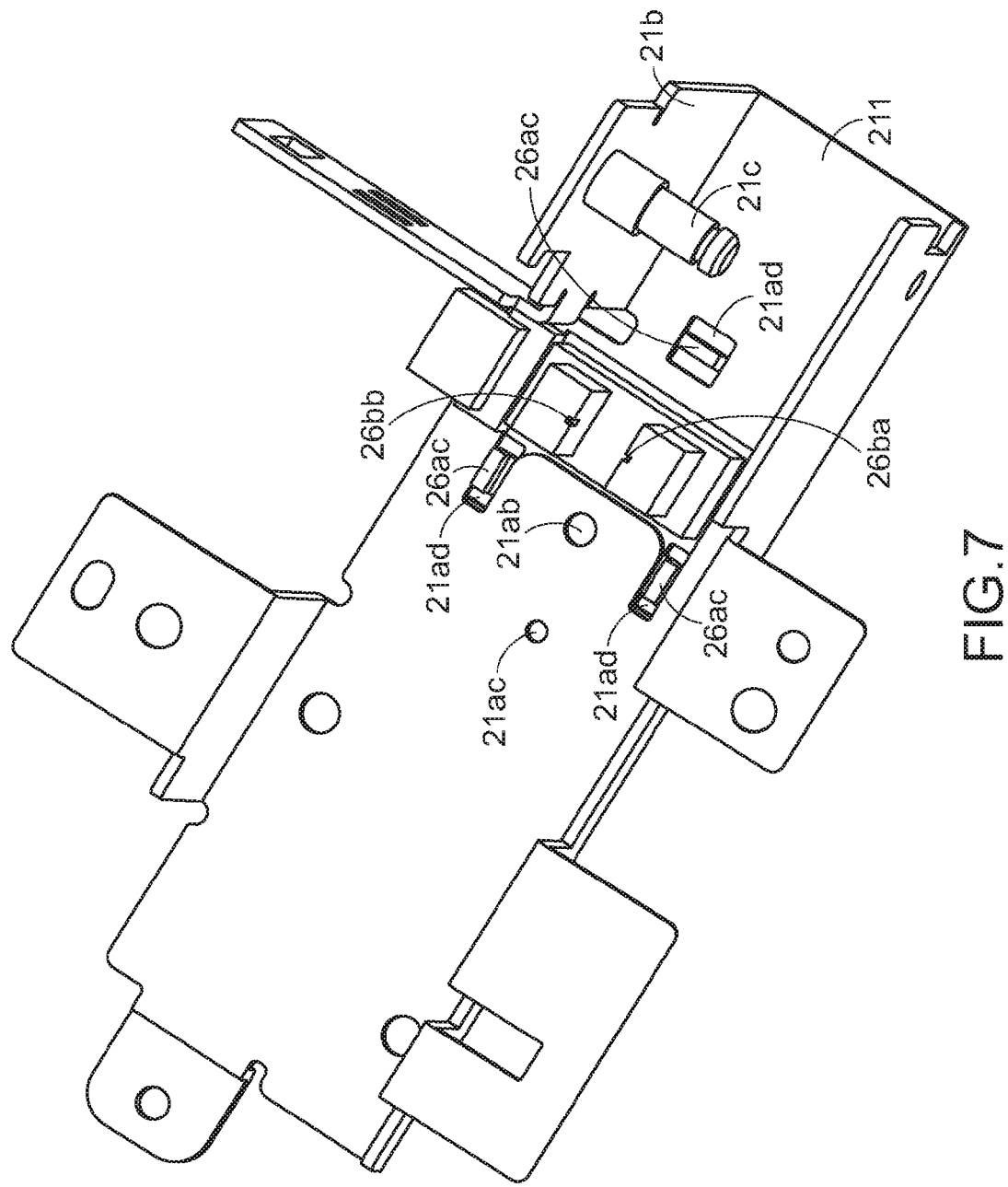
FIG. 7 is a schematic perspective view illustrating a combination of the bracket and the sensing device of the sheet thickness detection apparatus of FIG. 5 and taken along a first viewpoint.
Figure 8:
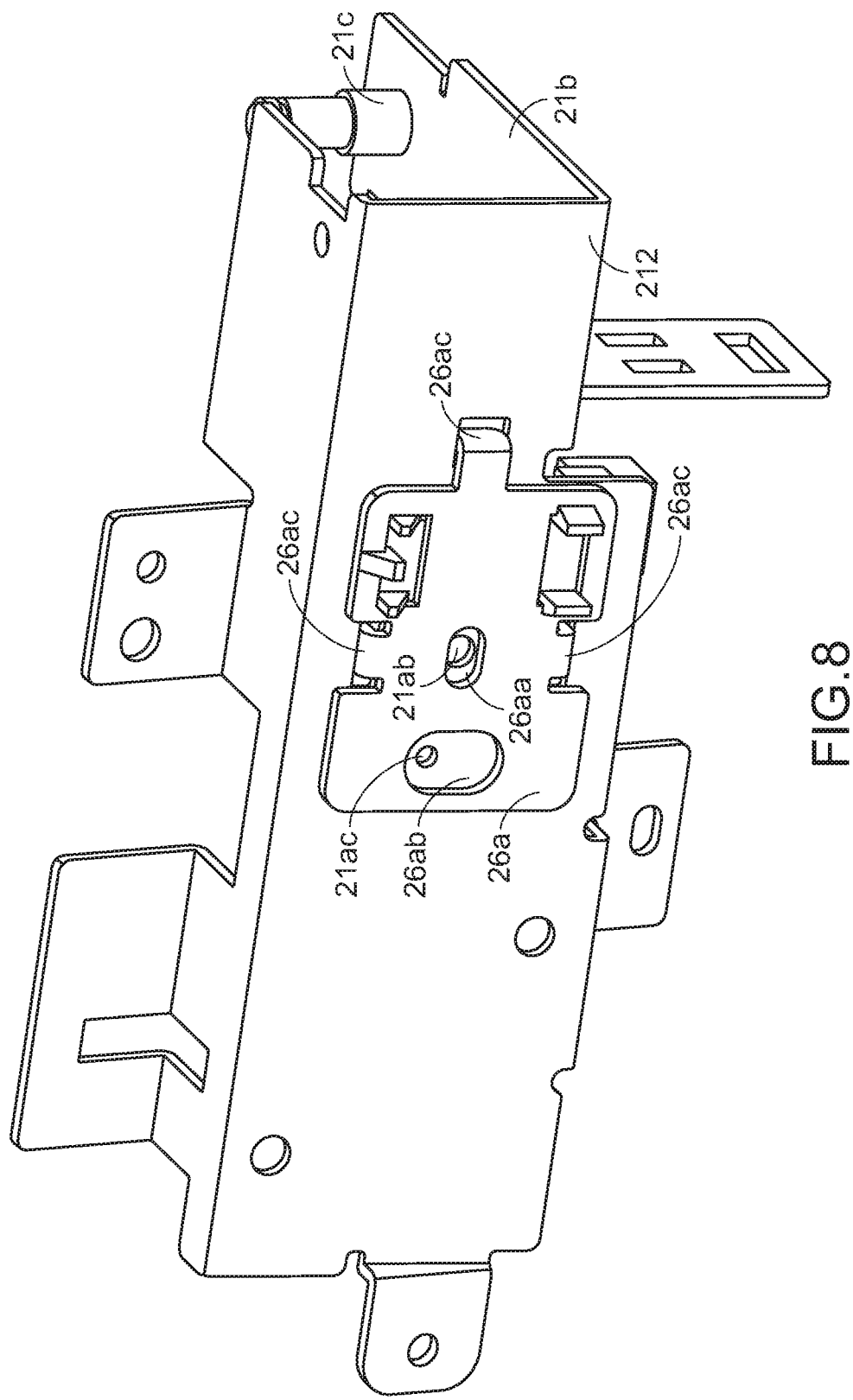
FIG. 8 is a schematic perspective view illustrating a combination of the bracket and the sensing device of the sheet thickness detection apparatus of FIG. 5 and taken along a second viewpoint.

Hereinafter, a sequence of assembling the conventional sheet thickness detection apparatus according to an embodiment of the present invention will be illustrated with reference to FIGS. 5, 6, 7 and 8. FIG. 6 is a schematic perspective view illustrating the sheet thickness detection apparatus of FIG. 5. FIG. 7 is a schematic perspective view illustrating a combination of the bracket and the sensing device of the sheet thickness detection apparatus of FIG. 5 and taken along a first viewpoint. FIG. 8 is a schematic perspective view illustrating a combination of the bracket and the sensing device of the sheet thickness detection apparatus of FIG. 5 and taken along a second viewpoint.

Firstly, the side plate 21b of the bracket 21 is perpendicular to the base 21a, the perforation 21aa is formed in the base 21a, the sliding grooves 21ad are arranged around the perforation 21aa, and the shaft 21c is protruded from the side plate 21b.

Then, the coil bobbin 22a is fixed on a first surface 211 of the base 21a. A first end 22ba of the plunger 22b is disposed within the channel 22aa of the coil bobbin 22a. A second end 22bb of the plunger 22b is exposed outside the coil bobbin 22a. Moreover, the positioning plate 22c is arranged around the second end 22bb of the plunger 22b.

Moreover, the first linking lever 23 is connected with the second end 22bb of the plunger 22b. A first end 24a of the second linking lever 24 is pivotally coupled to the first linking lever 23. A second end 24b of the second linking lever 24 is pivotally coupled to the shaft 21c of the bracket 21. Moreover, the sheet pressing part 25 is extended from the second end 24b of the second linking lever 24.

The elastic element 27 is sheathed around the shaft 21c. In addition, a distal end 27a of the elastic element 27 is sustained against the sheet pressing part 25.

Moreover, the sensor 26b is fixed on the supporting part 26a. When the three hooks 26ac of the supporting part 26a are embedded into the three sliding grooves 21ad of the base 21a from the second surface 212 of the base 21a, the sensor 26b is also penetrated through the perforation 21aa of the base 21a, so that the sensor 26b is exposed to bilateral sides of the first linking lever 23. Consequently, the emitting terminal 26ba and the receiving terminal 26bb of the sensor 26b are located at two opposite sides of the first linking lever 23, respectively. Moreover, the first fixing hole 26aa is overlapped with the second fixing hole 21ab, and the first adjusting hole 26ab is overlapped with the second adjusting hole 21ac.

Moreover, after a fixing element (not shown) is penetrated through the first fixing hole 26aa of the supporting part 26a and the second fixing hole 21ab of the base 21a, the supporting part 26a may be fixed on the second surface 212 of the base 21a. In an embodiment, the fixing element is a screw. For clearly describing the features of the present invention, the fixing element is not shown in the drawings.

As mentioned above, the first fixing hole 26aa of the supporting part 26a is elliptic. Consequently, the supporting part 26a may be moved relative to the fixing element and the base 21a. The movable ranges of the three hooks 26ac of the supporting part 26a are respectively limited by the three sliding grooves 21ad of the base 21a (see FIGS. 7 and 8). In such way, the supporting part 26a is only permitted to be moved in the direction parallel with the first linking lever 23. Moreover, since the sensor 26b is fixed on the supporting part 26a, the sensor 26b is moved with the supporting part 26a. In such way, the location of the sensor 26b relative to the first linking lever 23 is changed.

Figure 9:
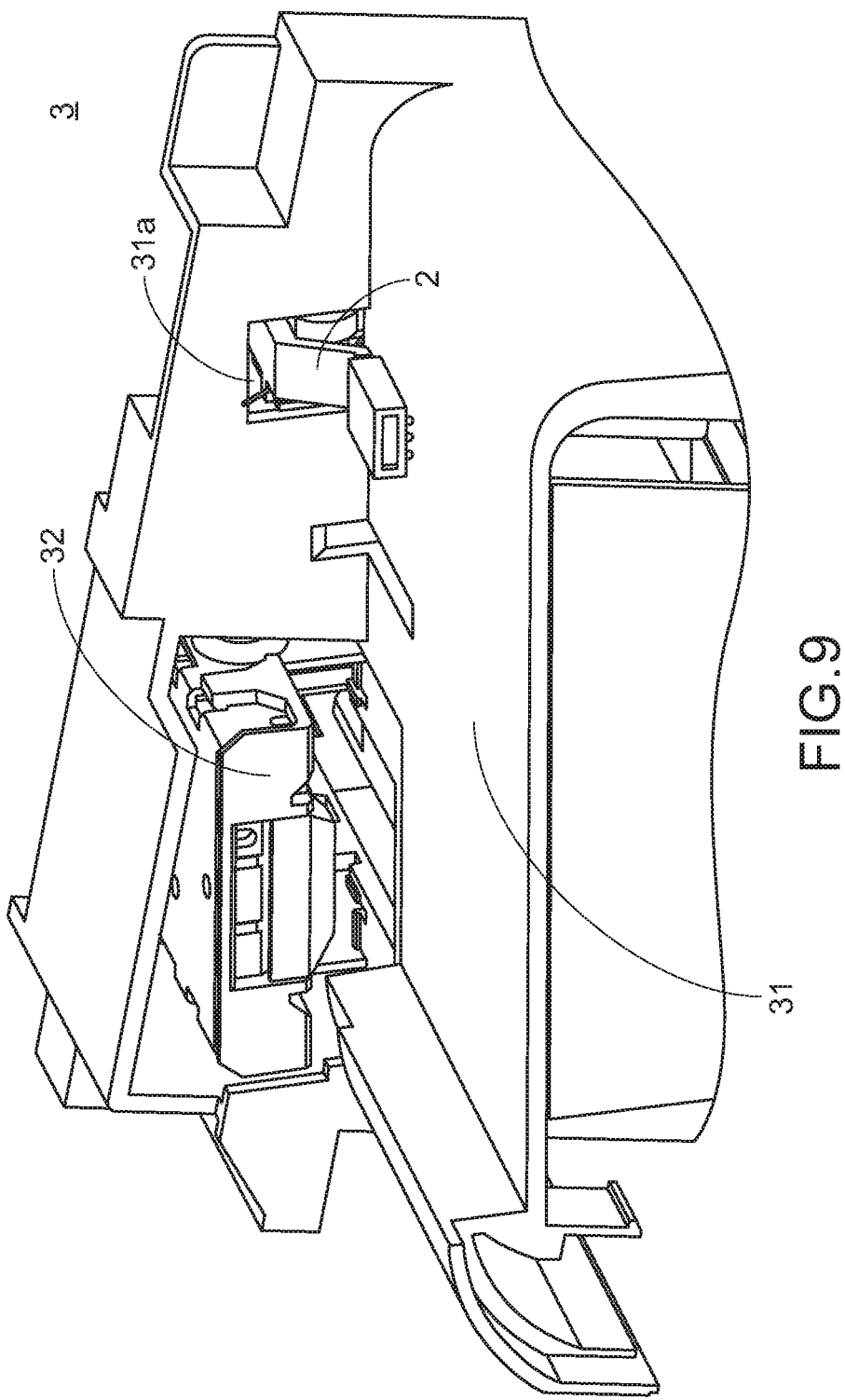
FIG. 9 is a schematic partial perspective view illustrating the present sheet thickness detection apparatus applied to a post-processing apparatus of an office machine.
Figure 10:
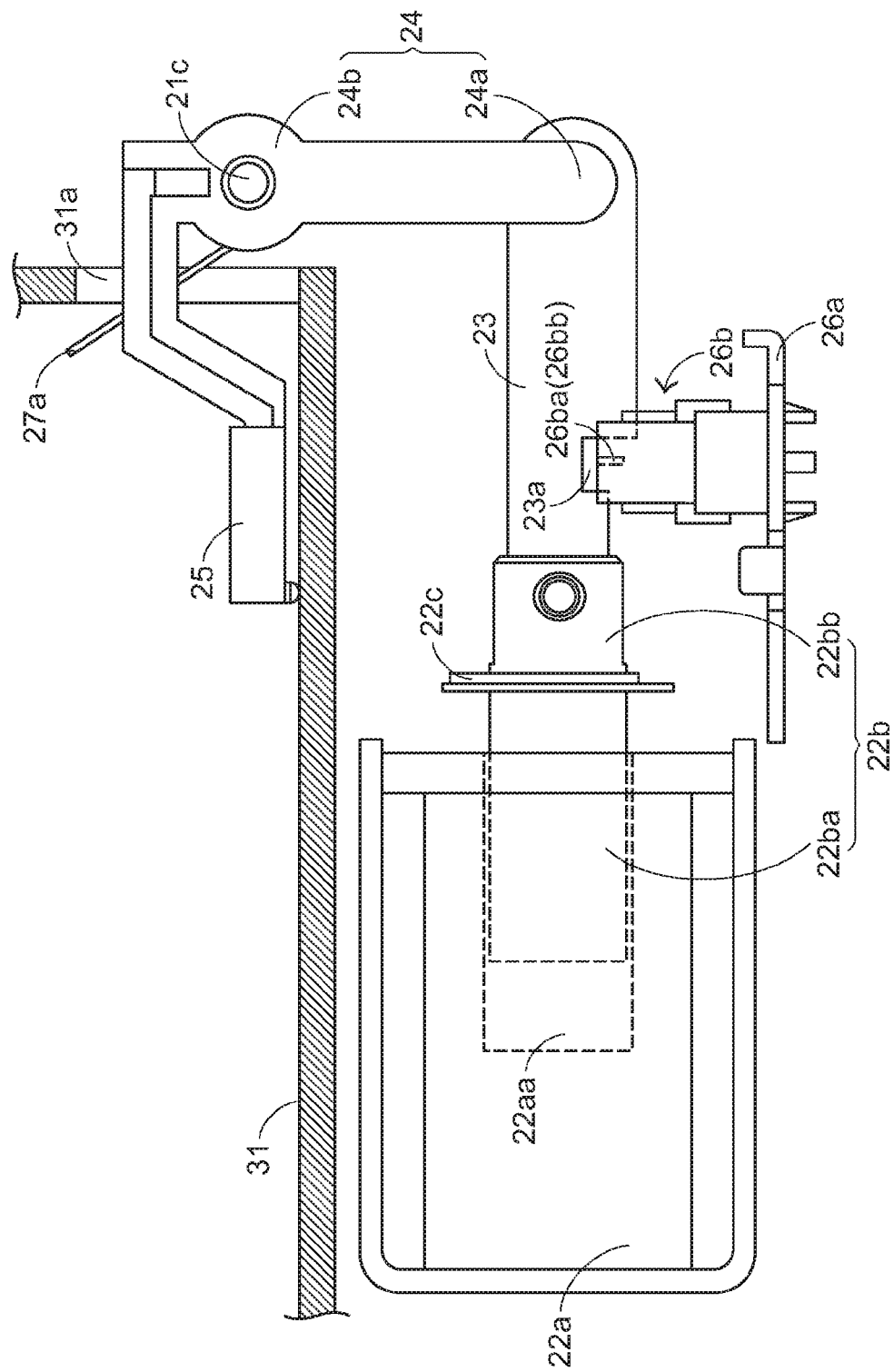
FIG. 10 is a schematic side view illustrating the present sheet thickness detection apparatus, in which no paper sheet is introduced into the sheet placement platform.
Figure 11:
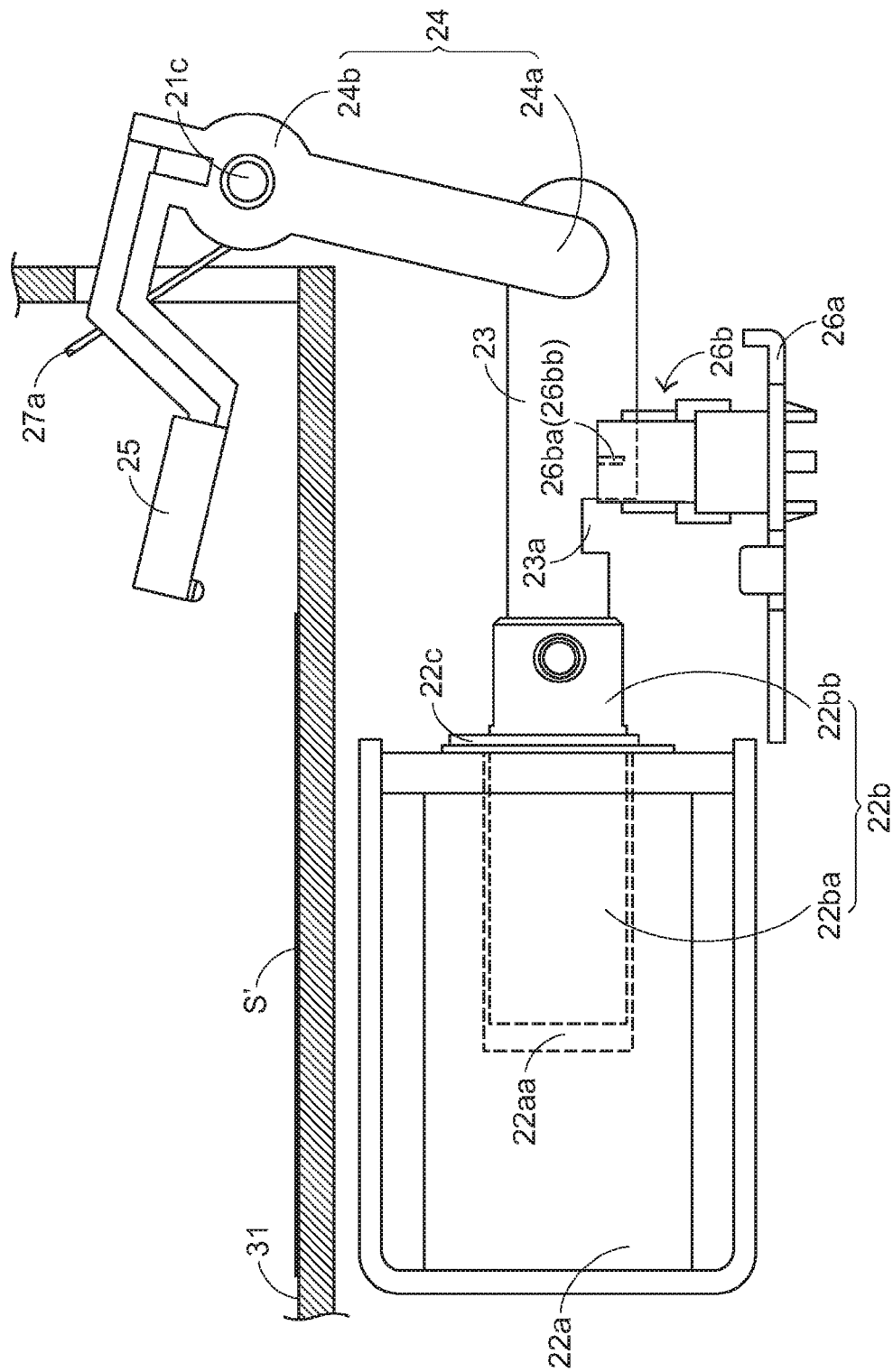
FIG. 11 is a schematic side view illustrating the present sheet thickness detection apparatus, in which the sensing device is in a first position and a paper sheet is about to be introduced into the sheet placement platform.
Figure 12:
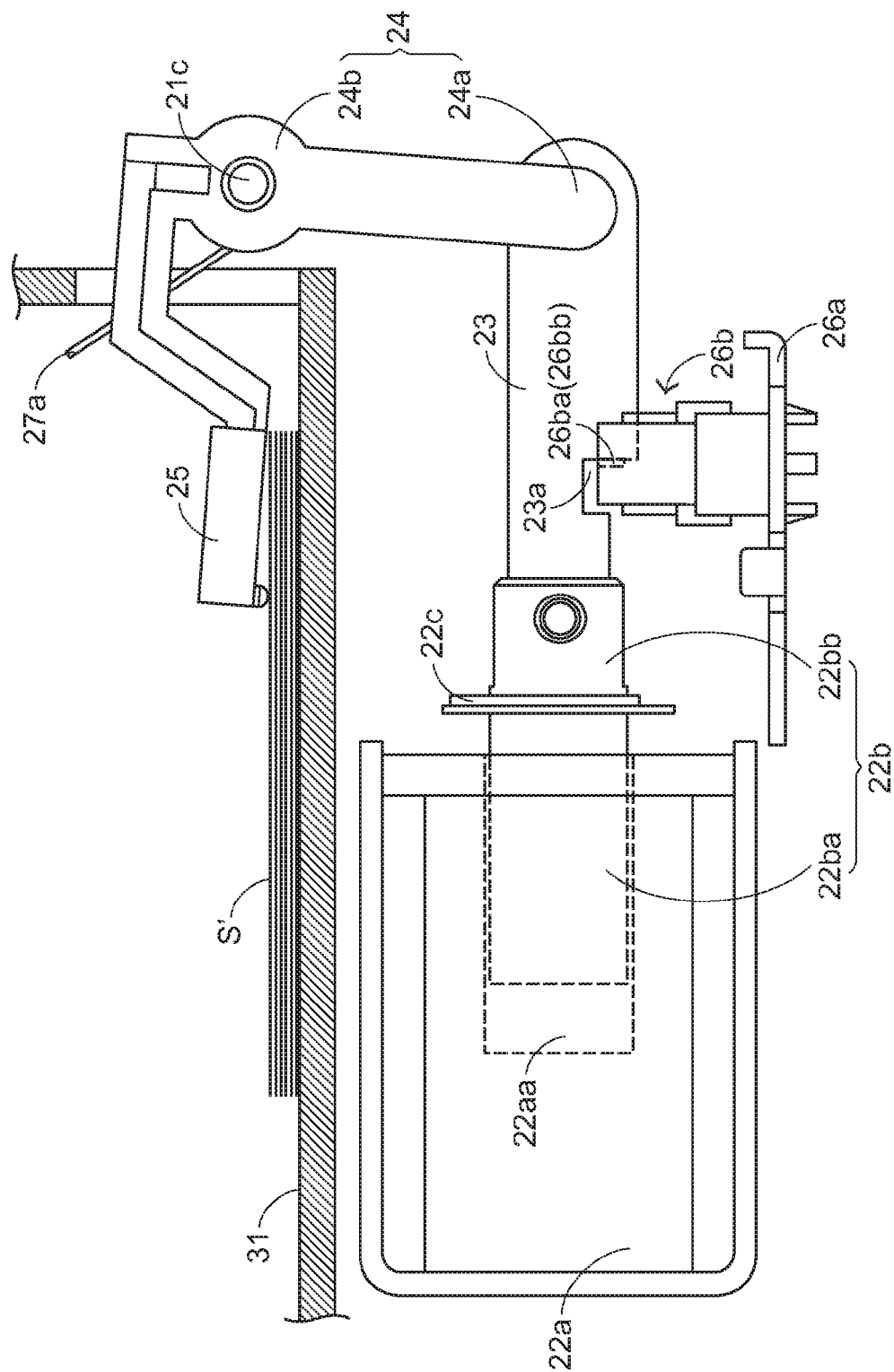
FIG. 12 is a schematic side view illustrating the present sheet thickness detection apparatus, in which the sensing device is in the first position and the thickness of plural paper sheets does not exceed a first maximum allowable thickness.
Figure 13:
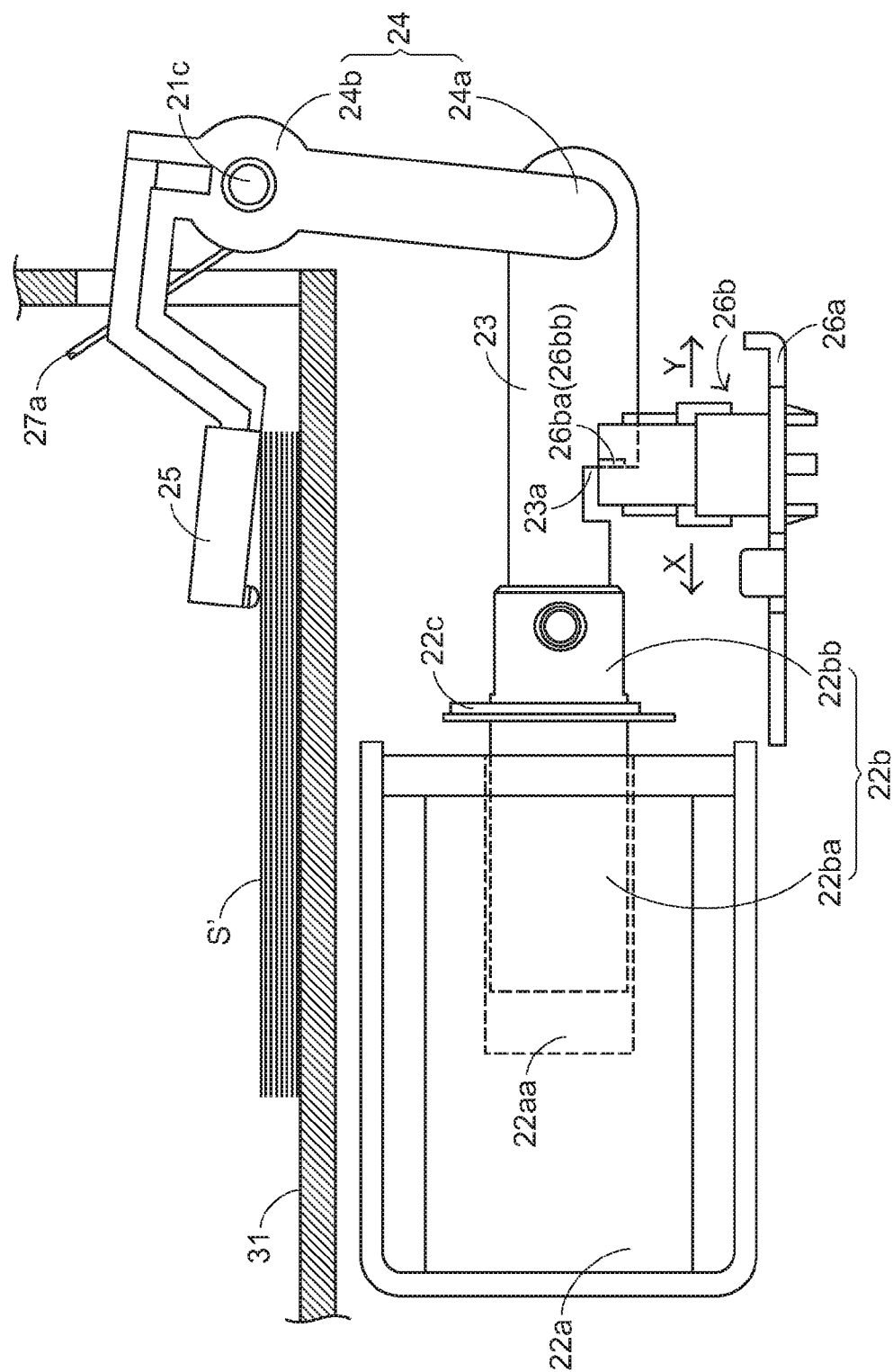
FIG. 13 is a schematic side view illustrating the present sheet thickness detection apparatus, in which the sensing device is in the first position and the thickness of plural paper sheets exceeds the first maximum allowable thickness.

Hereinafter, the operating principles of the sheet thickness detection apparatus according to an embodiment of the present invention will be illustrated with reference to FIGS. 9, 10, 11, 12 and 13. FIG. 9 is a schematic partial perspective view illustrating the present sheet thickness detection apparatus applied to a post-processing apparatus of an office machine. FIG. 10 is a schematic side view illustrating the present sheet thickness detection apparatus, in which no paper sheet is introduced into the sheet placement platform. FIG. 11 is a schematic side view illustrating the present sheet thickness detection apparatus, in which the sensing device is in a first position and a paper sheet is about to be introduced into the sheet placement platform. FIG. 12 is a schematic side view illustrating the present sheet thickness detection apparatus, in which the sensing device is in the first position and the thickness of plural paper sheets does not exceed a first maximum allowable thickness. FIG. 13 is a schematic side view illustrating the present sheet thickness detection apparatus, in which the sensing device is in the first position and the thickness of plural paper sheets exceeds the first maximum allowable thickness.

As shown in FIG. 9, the post-processing apparatus comprises a sheet placement platform 31 and a stapling apparatus 32. The majority of the sheet thickness detection apparatus 2 is disposed under the sheet placement platform 31. The sheet pressing part 25 of the sheet thickness detection apparatus 2 is penetrated through a slot 31a of the sheet placement platform 31, and exposed to the sheet placement platform 31.

Moreover, the stapling apparatus 32 is able to staple a stack of paper sheets with a limited thickness during each stapling cycle. Consequently, before the stapling operation is done, it is necessary to allow the sheet thickness detection apparatus 2 to judge whether the thickness of the paper sheets on the sheet placement platform 31 exceeds the maximum allowable thickness of the stapling apparatus 32 or not.

The post-processing apparatus of this embodiment is illustrated by referring to the post-processing apparatus 3 with the stapling apparatus 32. Alternatively, in some other embodiments, the post-processing apparatus 3 may include a punching apparatus or any other equipment for processing a stack of paper sheets with a thickness not exceeding a specified allowable thickness.

In this embodiment, it is assumed that the maximum thickness of the paper sheets to be stapled by the stapling apparatus 32 is a first maximum allowable thickness. In a case that no paper sheet is introduced into the sheet placement platform 31, the power device 22 is not driven by the controller (not shown), so that the first linking lever 23 and the second linking lever 24 are not moved. Under this circumstance, the distal end 27a of the elastic element 27 is sustained against the sheet pressing part 25, so that the sheet pressing part 25 is swung toward the sheet placement platform 31 to be attached on the sheet placement platform 31 (see FIG. 10).

At the same time, the second linking lever 24 is swung along with the sheet pressing part 25 relative to the shaft 21c, so that the first linking lever 23 and the plunger 22b are moved in the direction distant from the coil bobbin 22a.

When a paper sheet S' is about to be introduced into the sheet placement platform 31, the controller (not shown) may enable the power device 22. Consequently, the plunger 22b of the power device 22 is moved within the channel 22aa of the coil bobbin 22a until the positioning plate 22c is contacted with the coil bobbin 22a.

At the same time, the first linking lever 23 is pulled by the plunger 22b to be moved in the direction toward the coil bobbin 22a. Consequently, the second linking lever 24 is swung relative to the shaft 21c. Meanwhile, the sheet pressing part 25 is raised to be distant from the sheet placement platform 31 (see FIG. 11), and the paper sheet S' will be moved to the region under the sheet pressing part 25.

After the paper sheet S' is moved to the region under the sheet pressing part 25, the controller (not shown) disables the power device 22. Consequently, the second linking lever 24 is not moved with the first linking lever 23. Under this circumstance, the distal end 27a of the elastic element 27 is sustained against the sheet pressing part 25 again, so that the sheet pressing part 25 is swung toward the sheet placement platform 31 to press the paper sheet S'.

The above actions of the sheet thickness detection apparatus 2 are repeatedly done until the plural paper sheets S* to be stapled are all introduced into the region under the sheet pressing part 25.

As the number of the paper sheets S' is increased, the position of the sheet pressing part 25 pressing the plural paper sheets S' is gradually distant from the sheet placement platform 31. Consequently, the first linking lever 23 is pushed by the second linking lever 24 and gradually moved toward the coil bobbin 22a.

If the thickness of the plural paper sheets S' does not exceed the first maximum allowable thickness (see FIG. 12), the signal emitted by the emitting terminal 26ba of the sensor 26b can be transmitted to the receiving terminal 26bb of the sensor 26b through the notch 23a of the first linking lever 23. Under this circumstance, the controller (not shown) judges that the thickness of the plural paper sheets S' does not exceed the first maximum allowable thickness. Consequently, the controller will start the subsequent stapling operation.

On the other hand, if the thickness of the plural paper sheets S' exceeds the first maximum allowable thickness (see FIG. 13), the signal emitted by the emitting terminal 26ba of the sensor 26b is hindered by the first linking lever 23 and unable to be transmitted to the receiving terminal 26bb of the sensor 26b. Under this circumstance, the controller (not shown) judges that the thickness of the plural paper sheets S' exceeds the first maximum allowable thickness. Consequently, the controller will stop the stapling operation.

Figure 14:
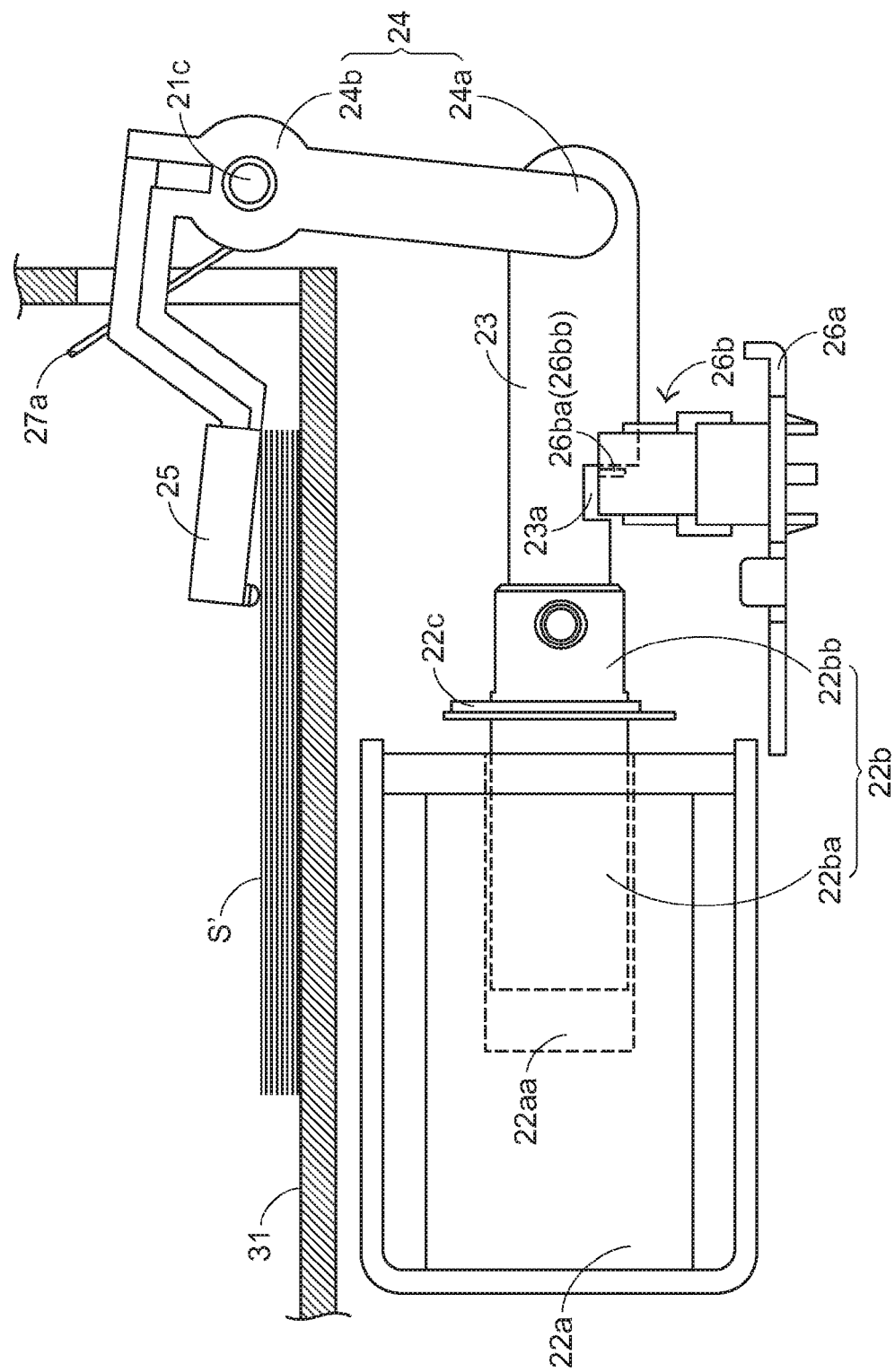
FIG. 14 is a schematic side view illustrating the present sheet thickness detection apparatus, in which the sensing device is in a second position and the thickness of plural paper sheets does not exceed a second maximum allowable thickness.
Figure 15:
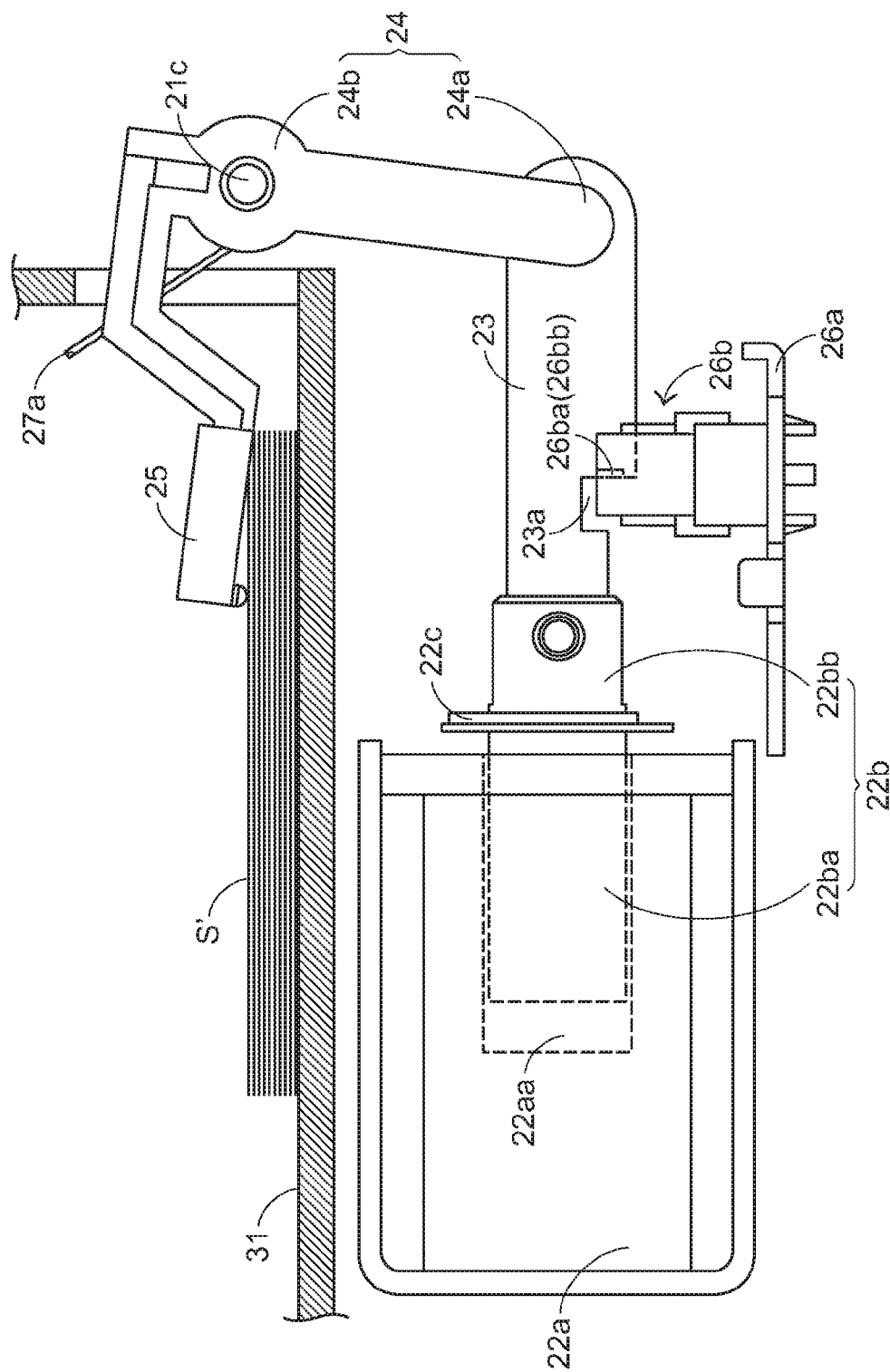
FIG. 15 is a schematic side view illustrating the present sheet thickness detection apparatus, in which the sensing device is in the second position and the thickness of plural paper sheets exceeds the second maximum allowable thickness.

Please refer to FIGS. 13, 14 and 15. FIG. 14 is a schematic side view illustrating the present sheet thickness detection apparatus, in which the sensing device is in a second position and the thickness of plural paper sheets does not exceed a second maximum allowable thickness. FIG. 15 is a schematic side view illustrating the present sheet thickness detection apparatus, in which the sensing device is in the second position and the thickness of plural paper sheets exceeds the second maximum allowable thickness.

As shown in FIG. 13, due to the thickness of the plural paper sheets S', the signal emitted by the emitting terminal 26ba of the sensor 26b is hindered by the first linking lever 23. Consequently, the controller (not shown) will stop the stapling operation.

In a case that the maximum thickness of the paper sheets to be stapled by the stapling apparatus 32 is changed to a second maximum allowable thickness greater than the first maximum allowable thickness, the sensor 26b may be moved in a first direction X by the user (see FIG. 13). Consequently, even if the number of the paper sheets S' is equal to the number of the paper sheets S' as shown in FIG. 13, the signal emitted by the emitting terminal 26ba of the sensor 26b is no longer hindered by the first linking lever 23 (see FIG. 14). Under this circumstance, only when the thickness of plural paper sheets S' exceeds the second maximum allowable thickness, the signal emitted by the emitting terminal 26ba of the sensor 26b may be hindered by the first linking lever 23 (see FIG. 15).

Similarly, in a case that the maximum thickness of the paper sheets to be stapled by the stapling apparatus 32 is changed to a third maximum allowable thickness smaller than the first maximum allowable thickness, the sensor 26b may be moved in a second direction Y by the user (see FIG. 13). Under this circumstance, if the thickness of plural paper sheets S' exceeds the third maximum allowable thickness, which is smaller than the first maximum allowable thickness as shown in FIG. 13, the signal emitted by the emitting terminal 26ba of the sensor 26b may be hindered by the first linking lever 23.

From the above discussions, the position of the sensor 26b of the sheet thickness detection apparatus 2 of the present invention can be adjusted according to the maximum allowable thickness of the paper sheets that can be stapled by the stapling apparatus 32. As a consequence, the sheet thickness detection apparatus 2 can accurately judge whether the thickness of the paper sheets exceeds the maximum allowable thickness or not.

Figure 16:
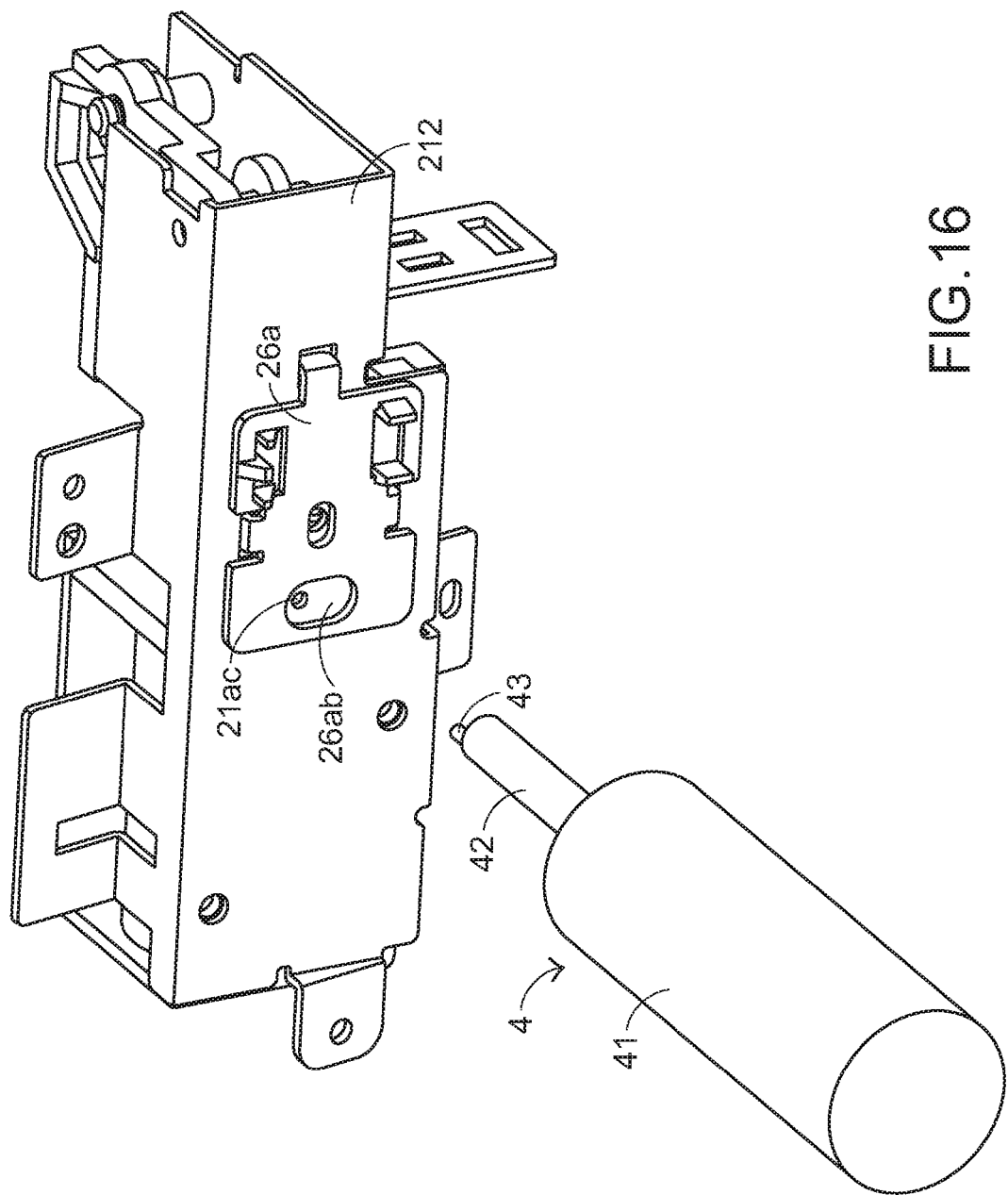
FIG. 16 is a schematic perspective view illustrating the relationship between the sheet thickness detection apparatus and an adjusting tool according to an embodiment of the present invention.

By the way, there are some approaches of moving the sensor 26b. Hereinafter, an approach of moving the sensor 26b will be illustrated with reference to FIG. 16. FIG. 16 is a schematic perspective view illustrating the relationship between the sheet thickness detection apparatus and an adjusting tool according to an embodiment of the present invention.

As shown in FIG. 16, the adjusting tool 4 comprises a handle 41, a first adjusting rod 42, and a second adjusting rod 43. The second adjusting rod 43 is extended from a tip of the first adjusting rod 42 (see FIG. 16).

For changing the position of the supporting part 26a, a spacer element having a thickness matching the maximum allowable thickness of the stapling apparatus is firstly interposed into the gap between the sheet placement platform 31 and the sheet pressing part 25 (see FIG. 9), and then the second adjusting rod 43 is inserted into the second adjusting hole 21ac of the base 21a.

Then, by rotating the handle 41, the first adjusting rod 42 is simultaneously rotated to push the inner periphery of the first adjusting hole 26ab. Meanwhile, the supporting part 26a and the sensor 26b are movable.

Until the emitting terminal 26ba of the sensor 26b is moved to a position where the signal emitted by the emitting terminal 26ba is just not hindered by the edge of the notch 23a of the first linking lever 23, the position-adjusting action of the supporting part 26a is completed.

In the above embodiments, the sensor is installed on a supporting part which is movable relative to the base. As a consequence, the sheet thickness detection apparatus can be modularized, and the sensor can be moved relative to the base.

Due to the modular design, the sheet thickness detection apparatus of the present invention can be directly applied to various office machines. Moreover, the sheet thickness detection apparatus can be installed in a simplified manner, and can be easily maintained and replaced.

Moreover, since the sensor is movable, the sheet thickness detection apparatus of the present invention can be applied to various post-processing apparatuses of different specifications. Regardless of the maximum allowable thickness that can be processed by the post-processing apparatus, it is only necessary to adjust the position of the sensing device without the need of replacing the sheet thickness detection apparatus.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A sheet thickness detection apparatus for detecting a thickness of plural paper sheets on a sheet placement platform, said sheet thickness detection apparatus having a maximum allowable thickness, said sheet thickness detection apparatus comprising:
   a bracket comprising a base with a perforation;
   a power device fixed on a first surface of said base;
   a first linking lever connected with said power device and driven by said power device to be moved, wherein said first linking lever has a notch;
   a second linking lever having a first end and a second end, wherein as said first linking lever is moved, said second linking lever is correspondingly swung, wherein said first end of said second linking lever is pivotally coupled with said first linking lever;
   a sheet pressing part extended from said second end of said second linking lever and simultaneously swung with said second linking lever; and
   a sensing device comprising a supporting part and a sensor, wherein said supporting part is connected to a second surface of said base, wherein said sensor is fixed on said supporting part and penetrated through said perforation from said second surface of said base, so that said sensor is exposed to a lateral side of said first linking lever to detect whether said thickness of said plural paper sheets exceeds said maximum allowable thickness or not, wherein said supporting part comprises three hooks, and said base further comprises three sliding grooves, wherein when said supporting part is connected with said base, said three hooks are respectively embedded into said three sliding grooves, so that said supporting part is only permitted to be moved in a direction parallel with said first linking lever,
   wherein by moving said supporting part, said sensor is moved to a position where said maximum allowable thickness is detectable.

2. The sheet thickness detection apparatus according to claim 1, wherein when said first linking lever is driven by said power device to be moved in a first direction, said second linking lever is linked by said first linking lever, so that said sheet pressing part is swung in a direction distant from said sheet placement platform.

3. The sheet thickness detection apparatus according to claim 1, further comprising an elastic element, wherein a distal end of said elastic element is sustained against said sheet pressing part.

4. The sheet thickness detection apparatus according to claim 3, wherein when said first linking lever is not driven by said power device, said sheet pressing part is swung in a direction distant toward said sheet placement platform through said elastic element.

5. The sheet thickness detection apparatus according to claim 4, wherein said sensor comprises an emitting terminal and a receiving terminal, wherein said emitting terminal and said receiving terminal are located at two opposite sides of said first linking lever, respectively.

6. The sheet thickness detection apparatus according to claim 5, wherein when said plural paper sheets on said sheet placement platform are pressed by said sheet pressing part, if said thickness of plural paper sheets does not exceed said maximum allowable thickness, a signal emitted by said emitting terminal of said sensor is transmitted to said receiving terminal of said sensor through said notch of said first linking lever.

7. The sheet thickness detection apparatus according to claim 6, wherein when said plural paper sheets on said sheet placement platform are pressed by said sheet pressing part, if said thickness of plural paper sheets exceeds said maximum allowable thickness, said signal emitted by said emitting terminal of said sensor is hindered by said first linking lever.

8. The sheet thickness detection apparatus according to claim 1, wherein said bracket further comprises:
 a side plate perpendicular to said base; and
 a shaft protruded from said side plate, wherein said second end of said second linking lever is pivotally coupled to said shaft, and said second linking lever is permitted to be swung relative to said shaft.

9. The sheet thickness detection apparatus according to claim 1, wherein said power device comprises:
 a coil bobbin fixed on said first surface of said base, and having a channel;
 a plunger having a first end accommodated within said channel and a second end exposed outside said coil bobbin; and
 a positioning plate arranged around said second end of said plunger.

10. The sheet thickness detection apparatus according to claim 9, wherein said first linking lever is connected with said second end of said plunger.

11. The sheet thickness detection apparatus according to claim 1, wherein said sheet pressing part is integrally formed with said second linking lever, and an included angle between said sheet pressing part and said second linking lever is approximately 90 degrees.

12. A sheet thickness detection apparatus for detecting a thickness of plural paper sheets on a sheet placement platform, said sheet thickness detection apparatus having a maximum allowable thickness, said sheet thickness detection apparatus comprising:
 a bracket comprising a base with a perforation;
 a power device fixed on a first surface of said base;
 a first linking lever connected with said power device and driven by said power device to be moved, wherein said first linking lever has a notch;
 a second linking lever having a first end and a second end, wherein as said first linking lever is moved, said second linking lever is correspondingly swung, wherein said first end of said second linking lever is pivotally coupled with said first linking lever;
 a sheet pressing part extended from said second end of said second linking lever and simultaneously swung with said second linking lever; and
 a sensing device comprising a supporting part and a sensor, wherein said supporting part is connected to a second surface of said base, wherein said sensor is fixed on said supporting part and penetrated through said perforation from said second surface of said base, so that said sensor is exposed to a lateral side of said first linking lever to detect whether said thickness of said plural paper sheets exceeds said maximum allowable thickness or not, wherein said supporting part has a first fixing hole and a first adjusting hole, wherein said first fixing hole and said first adjusting hole are both elliptic.

13. The sheet thickness detection apparatus according to claim 12, wherein said base further comprises:
 a second fixing hole overlapped with said first fixing hole, so that said supporting part is connected to said second surface of said bracket through said first fixing hole and said second fixing hole; and
 a second adjusting hole overlapped with said first adjusting hole.

14. The sheet thickness detection apparatus according to claim 12, wherein when said first linking lever is driven by said power device to be moved in a first direction, said second linking lever is linked by said first linking lever, so that said sheet pressing part is swung in a direction distant from said sheet placement platform.

15. The sheet thickness detection apparatus according to claim 12, further comprising an elastic element, wherein a distal end of said elastic element is sustained against said sheet pressing part.

16. The sheet thickness detection apparatus according to claim 15, wherein when said first linking lever is not driven by said power device, said sheet pressing part is swung in a direction distant toward said sheet placement platform through said elastic element.

17. The sheet thickness detection apparatus according to claim 16, wherein said sensor comprises an emitting terminal and a receiving terminal, wherein said emitting terminal and said receiving terminal are located at two opposite sides of said first linking lever, respectively.

18. The sheet thickness detection apparatus according to claim 17, wherein when said plural paper sheets on said sheet placement platform are pressed by said sheet pressing part, if said thickness of plural paper sheets does not exceed said maximum allowable thickness, a signal emitted by said emitting terminal of said sensor is transmitted to said receiving terminal of said sensor through said notch of said first linking lever.

19. The sheet thickness detection apparatus according to claim 18, wherein when said plural paper sheets on said sheet placement platform are pressed by said sheet pressing part, if said thickness of plural paper sheets exceeds said maximum allowable thickness, said signal emitted by said emitting terminal of said sensor is hindered by said first linking lever.

20. The sheet thickness detection apparatus according to claim 12, wherein said bracket further comprises:
 a side plate perpendicular to said base; and
 a shaft protruded from said side plate, wherein said second end of said second linking lever is pivotally coupled to said shaft, and said second linking lever is permitted to be swung relative to said shaft.

* * * * *